United States Patent [19]

Shaw

[11] Patent Number: 5,530,163

[45] Date of Patent: Jun. 25, 1996

[54] PROCESS FOR PRODUCING ORGANIC POLYSULFIDE COMPOUNDS

[75] Inventor: James E. Shaw, Bartlesville, Okla.

[73] Assignee: Phillips Petroleum Company, Bartlesville, Okla.

[21] Appl. No.: 377,064

[22] Filed: Jan. 23, 1995

[51] Int. Cl.$^6$ .................................................. C07C 321/00
[52] U.S. Cl. .................................................. 568/26
[58] Field of Search .................................................. 568/26

[56] References Cited

U.S. PATENT DOCUMENTS

| | | | |
|---|---|---|---|
| 3,308,166 | 3/1967 | Biensan et al. | 260/608 |
| 3,392,201 | 7/1968 | Warner | 260/608 |
| 4,564,709 | 1/1986 | Koyama et al. | 568/26 |
| 4,937,385 | 6/1990 | Buchholz et al. | 568/26 |
| 5,206,439 | 4/1993 | Shaw | 568/21 |
| 5,218,147 | 6/1993 | Shaw | 568/21 |
| 5,232,623 | 8/1993 | Shaw | 252/183.12 |

OTHER PUBLICATIONS

Vineyard, B. D., The Versatility and the Mechanism of the n–Butylamine–Catalyzed Reaction of Thiols with Sulfur, J. Org. Chem., Dec. 1967, pp. 3833–3836.

Primary Examiner—Paul J. Killos
Attorney, Agent, or Firm—Lucas K. Shay

[57] ABSTRACT

A process which can be used to produce organic polysulfide compounds is provided. The process comprises contacting, in the presence of a catalyst, a mercaptan with sulfur under conditions sufficient to produce an organic polysulfide and thereafter, the resulting reaction medium is contacted with an acid to produce an acid-treated organic polysulfide wherein the mercaptan, sulfur, and catalyst are each present in an amount effective to produce an organic polysulfide. The acid-treated organic polysulfide can be purified and recovered.

22 Claims, No Drawings

PROCESS FOR PRODUCING ORGANIC POLYSULFIDE COMPOUNDS

FIELD OF THE INVENTION

The present invention relates to a process for producing organic polysulfide compounds.

BACKGROUND OF THE INVENTION

Organic polysulfides containing two to five or even more sulfur atoms per molecule have been found useful for many purposes such as additives for elastomers, antioxidants for lubricating oils, intermediates for the production of organic chemicals, insecticides, germicides and as additives to diesel fuels to improve the octane number and ignition qualities of these fuels. These compounds have also been found useful in the compounding of extreme pressure lubricants and in the acceleration of rubber treating processes.

Such polysulfide compounds can be prepared by reacting mercaptans with elemental sulfur in the presence of a basic catalyst. For example, Biensan et al (U.S. Pat. No. 3,308,166) discloses that polysulfides can be prepared from a mercaptan and sulfur catalyzed by an amine using an alcohol promoter.

A conventional process for producing an organic polysulfide compound such as di-t-butyl trisulfide is to react a mercaptan such as t-butylmercaptan with elemental sulfur in the presence of a basic catalyst. However, the polysulfide thus prepared is generally associated with some unreacted mercaptans and residual $H_2S$ contributing to unpleasant odor. Additionally, possibly because of the unreacted mercaptans, the product always becomes very unstable, i.e., the product turns cloudy, probably due to degradation of the polysulfide causing precipitation of sulfur. The instability along with the unpleasant odor greatly reduce the desirability and utility of polysulfide products.

It has also been shown that organic polysulfide compounds cause metal corrosion partly due to the presence of polysulfide compounds having four or more sulfur atoms. A small quantity of these polysulfide compounds having four or more sulfur atoms are always present when a polysulfide compound having less than four sulfur atoms is prepared. Therefore, there is need to develop an improved process for producing an organic polysulfide compound.

SUMMARY OF THE INVENTION

An object of the present invention is to provide a process for producing organic polysulfide compounds. Another object of the invention is to provide a process for producing organic polysulfide compounds under mild conditions. A further object of the present invention is to develop a process which produces an organic polysulfide compound that does not cause decomposition of the organic polysulfide compound during further processing or purification of the compound. Still another object of the invention is to produce an organic trisulfide compound. Yet still a further object of the present invention is to provide a simple and cost effective process for producing organic polysulfides which do not require an extensive distillation to purify the organic polysulfide. One of the advantages of the present invention is that an organic polysulfide, especially an organic trisulfide, can be produced in high yield at a mild condition. Another advantage is that an organic trisulfide produced by the present invention is less corrosive toward a metal. Other objects and advantages will become more apparent as the invention is more fully disclosed hereinbelow.

According to the present invention, a process which can be used to produce organic polysulfide compounds is provided. The process comprises contacting, in the presence of a catalyst, a mercaptan with sulfur under conditions sufficient to produce a crude organic polysulfide compound and, thereafter, the crude organic polysulfide compound is contacted with an acids; wherein the mercaptan, sulfur, and catalyst are each present in an amount effective to produce a crude organic polysulfide and the acid is present in an amount sufficient to effect the preparation of a stable organic polysulfide compound.

DETAILED DESCRIPTION OF THE INVENTION

According to the present invention, an organic polysulfide compounds having the formula of $R-S_q-R$, wherein each R can be the same or different and are each a hydrocarbyl radical having 1 to about 30, preferably about 1 to about 20, and most preferably 2 to 15 carbon atoms and q is a number from 2 to about 10, preferably 2 to 8, more preferably 3 to 5, and most preferably 3, can be produced by the process of the present invention. The hydrocarbyl radical can be linear or branched and can be alkyl, aryl, cycloalkyl, alkaryl, aralkyl, alkenyl radicals, or combinations of any two or more thereof. Preferably the hydrocarbyl radical is an alkyl radical. The presently most preferred organic sulfide compound is di-t-butyl polysulfide.

The term "stable organic polysulfide" or "stable organic polysulfide compound" used in the present application, unless otherwise indicated, denotes an organic polysulfide compound which does not substantially or significantly change the number of sulfur atoms per molecule of the organic polysulfide, or which has reduced susceptibility to decomposition, when the organic polysulfide is further processed by a physical treatment. The physical treatment can include purification, separation, recovery, or combination of two or more thereof. Examples of such physical treatments include, but are not limited to, distillation, gas sparging, mixing, heating, chromatographic separation, and combinations of any two or more thereof. For example, a stable organic trisulfide is an organic polysulfide compound, when it is processed such as, for example, distilled under reduced pressure, is not substantially or significantly decomposed to an organic disulfide or does not substantially or significantly increase the sulfur atoms in the trisulfide to, for example, tetrasulfide or pentasulfide.

According to the present invention, a process for producing an organic polysulfide is provided which comprises contacting a mercaptan with elemental sulfur in the presence of a catalyst wherein said catalyst can be any catalyst that is known to or can catalyze the reaction of a mercaptan and sulfur to form an organic polysulfide compound as defined hereinabove. The presently preferred catalyst comprises a basic catalyst which can be an inorganic base, an organic base, or combinations of two or more thereof.

Suitable organic bases include, but are not limited to, tetramethylammonium hydroxide, tetraethylammonium hydroxide, tetrapropylammonium hydroxide, tetramethylammonium bisulfide, tetraethylammonium bisulfide, trimethylamine, triethylamine, n-butylamine and combinations of any two or more thereof. Suitable inorganic bases include, but are not limited to, lithium hydroxide, sodium hydroxide, sodium bisulfide, potassium hydroxide, calcium hydroxide, magnesium hydroxide, sodium bicarbonate, sodium carbonate, sodium oxide, sodium sulfide, magnesium oxide, calcium oxide, calcium carbonate, sodium phenoxide, barium phenoxide, calcium phenoxide, $R^1ONa$, $R^1SNa$, and combinations of any two or more thereof; where $R^1$ is a $C_1$–$C_{18}$ alkyl radical, or combinations of any two or more thereof. Presently, the amine catalysts are not as preferred as other catalysts and an inorganic base is preferred because of availability and low cost of inorganic bases. Among the inorganic bases, sodium hydroxide is preferred because it is readily available and inexpensive.

The catalyst useful in the production of an organic polysulfide can also comprise an alkoxylated compound which is selected from alkoxylated alcohols, alkoxylated mercaptans, and combinations of any two or more thereof.

The alkoxylated alcohol useful in the present invention has a general formula of $R^2O[CH_2CH(R^3)O]_mH$ where $R^2$ is a $C_1$–$C_{20}$ hydrocarbyl radical selected from the group consisting of alkyl radical, alkylaryl radical, aryl radical, cycloalkyl radical and alkenyl radical; Preferably $R^2$ is a $C_6$–$C_{18}$ alkyl radical. Most preferably $R^2$ is a $C_{10}$–$C_{16}$ alkyl radical; $R^3$ is selected from the group consisting of hydrogen, $C_1$–$C_{16}$ alkyl radicals, and $C_2$–$C_{16}$ alkenyl radicals; and n is a number of from 1 to about 20, preferably from about 2 to about 12, most preferably from 5 to 10. Generally $R^3$ can contain from 0 to about 16 carbon atoms. Preferably $R^3$ is a hydrogen or a $C_1$–$C_3$ alkyl radical. Most preferably $R^3$ is hydrogen. An example of suitable alkoxylated alcohol is TERGITOL 15-S-7 which is an ethoxylated alcohol, is manufactured and marketed by Union Carbide Corporation, and has the formula of $R^2O(CH_2CH_2O)_7H$ where $R^2$ is a secondary alkyl radical having 11–15 carbon atoms and 7 is the averaged number of the ethylene oxide units. Another example is an ethoxylated phenol having the same number of ethylene oxide units. Other suitable alkoxylated alcohols are also available from Union Carbide Corporation.

The alkoxylated mercaptan useful in the present invention has a general formula of $R^2S[CH_2CH(R^3)O]_nH$ where $R^2$ and $R^3$ are the same as those described above. An example of an alkoxylated mercaptan is an ethoxylated mercaptan having the formula of $R^2S(CH_2CH_2O)_7H$ where $R^2$ is primarily a tertiary dodecyl group and 7 is the averaged number of ethylene oxide units. This ethoxylated mercaptan is a surfactant, commercially available from Phillips Petroleum Company, Bartlesville, Okla. under the trade name AQUA-CLEEN® II. Another example is an ethoxylated thiophenol having the same number of ethylene oxide units. Other suitable alkoxylated mercaptans are also available from Phillips Petroleum Company.

The weight ratio of a base to an alkoxylated alcohol, or an alkoxylated mercaptan can vary widely so long as the ratio can catalyze the reaction of mercaptan and sulfur, preferably from about 1:1 to about 1:100, most preferably from about 1:5 to about 1:20 for best results. If a mixture of bases is used, the weight ratio can be any ratio that catalyzes the reaction of mercaptan and sulfur and can be in the range of 1:1 to 999:1 for each base.

The catalyst used in the present invention, if containing a combination of bases and/or alkoxylated compounds, can be made by properly mixing the components in the ratio described above and employing any suitable mixing means such as shaking or stirring. The preparation can also be done in-situ, i.e., mixing the components of the catalyst in a medium containing a mercaptan and sulfur. The preparation of such catalyst has been disclosed in U.S. Pat. No. 5,232,623, disclosure of which is incorporated herein by reference.

The polysulfide can be prepared by the reaction of mercaptans having the formula of RSH and elemental sulfur catalyzed by a catalyst. The reaction is depicted as RSH+RSH+(q-1)S→$RS_qR$+$H_2S$ where each R and q are the same as those described above. The reaction can be carried out in any suitable reaction vessel. The choice of reaction vessel is a matter of preference to those skilled in the art.

Although any mercaptans having the formula of RSH can be employed in the present invention, the presently preferred mercaptans are tertiary mercaptans. The presently most preferred mercaptan is t-butyl mercaptan.

Conditions for contacting mercaptans with elemental sulfur are any suitable conditions that can result in the production of an organic polysulfide compound and can include a temperature in the range of from about 20° C. to about 250° C., preferably from 50° C. to 150° C., for a time of from about 10 minutes to about 10 hours, preferably 30 minutes to 5 hours. The pressure can vary widely from about 1 atmosphere to about 30 atmospheres, preferably from about 1 atmosphere to about 3 atmospheres.

Generally, one of the reactants, either the mercaptan or sulfur, is slowly added to the other reactant in the presence of the catalyst described above. The sulfur, upon addition, readily dissolves in the solution. Mixing of the solution and/or operating at higher than ambient temperatures will enhance the reaction rate. The amount of sulfur added depends on the desired sulfur content of the polysulfide product. For an average sulfur content of q sulfurs per polysulfide molecule, (q-1) moles of sulfur must be added per 2 moles of mercaptan and 1 mole of hydrogen sulfide will be released per 2 moles of mercaptans reacted. It is, however, preferred that about 0.5 to about 10, more preferably about 1.0 to about 5, and most preferably 1.0 to 2.0 moles of mercaptan per 1 mole of elemental sulfur is used. The weight of the catalyst as a percentage of the weight of mercaptans is a percentage that can catalyze the formation of an organic polysulfide and can be in the range of from 0.001 to 10%, preferably about 0.01 to 3%, and most preferably 0.05 to 2%.

Under the above-described suitable conditions, a reaction medium containing a desired crude polysulfide is formed. The reaction medium containing the crude organic polysulfide is then contacted with an amount of an acid that is effective to produce a stable organic polysulfide that has reduced susceptibility to distillation. Generally the amount can be in the range of from about 0.5 to about 2.0, preferably about 0.75 to about 1.5, and more preferably 0.9 to 1.1 equivalents of the base used as catalyst. Most preferably, the amount of acid is a neutralizing amount, i.e., an amount equal to the equivalents of the base used as catalyst, that brings the pH of the reaction medium to about 7 as if the reaction were an aqueous system.

The contacting of the reaction medium with an acid can be carried out under any conditions that is effective to produce a stable polysulfide or that can reduce the susceptibility of the organic polysulfide to decomposition during heating, during distillation of unreacted mercaptan, or sparging, of the reaction medium. Such conditions can be the same conditions employed for contacting mercaptans with elemental sulfur, as disclosed above.

The contacting of the reaction medium with an acid is preferably carried out before the removal of the residual hydrogen sulfide, though it can be carried out immediately after the removal of the residual hydrogen sulfide. However, such contacting is carried out before the reaction medium is heated. For example, the reaction medium is contacted with an acid before the reaction is distilled to remove unreacted mercaptan and later sparging with nitrogen. Residual hydrogen sulfide formed is generally removed from the crude organic polysulfide product by either an inert gas purge or by vacuum stripping. When using an inert gas purge, preferable gases are nitrogen and air. Thereafter, if necessary, the organic polysulfide product can be further stabilized using any known methods such as, for example, those disclosed in the U.S. Pat. Nos. 5,206,439; and 5,218,147, disclosures of which are incorporated herein by reference.

The acid useful in the present invention can be any acid so long as the acid can produce a stable organic polysulfide or reduce the susceptibility of an organic polysulfide to decomposition during a physical treatment such as, for example, distillation as disclosed above. Generally, the acid can be organic acids, inorganic acids, or combinations of any two or more thereof. The acid can also be a diluted aqueous acid solution. Examples of suitable acids include, but are not limited to sulfuric acid, hydrochloric acid, nitric acid, phosphoric acid, formic acid, acetic acid, trifluoroacetic acid, citric acid, trichloroacetic acid, p-toluenesulfonic acid, methanesulfonic acid, partially neutralized acids wherein one or more protons have been replaced with, for example, a metal, and combinations of any two or more thereof. Examples of partially neutralized acids include, but are not limited to, sodium bisulfate, sodium dihydrogen phosphate, potassium hydrogen tartarate, and combinations thereof.

The acid-treated, or stable, organic polysulfide compound can be further processed such as purification, separation, recovery, or combinations of any two or more thereof by any methods known to one skilled in the art such as, for example, distillation. Thereafter, if necessary, the organic polysulfide product can be further stabilized using any known methods such as, for example, those disclosed in the U.S. Pat. Nos. 5,206,439; and 5,218,147, disclosures of which are incorporated herein by reference.

The process of the invention can also be carried out continuously. For example, the contacting of mercaptans with elemental sulfur in the process of the invention catalyst can be done by employing continuous stir tank reactors connected in series, packed columns or towers in which the invention catalyst is supported on a solid support, and other continuous flows that are readily within the realm of one skilled in the art.

The organic polysulfide compounds can be purified and/or recovered by any methods known to one skilled in the art such as distillation.

The following examples are provided to further illustrate the practice of the invention and are not intended to limit the scope of the invention of the claims.

EXAMPLE I

This example illustrates the preparation of di-t-butyl trisulfide.

To a 500 ml, 3-necked flask equipped with thermowell, magnetic stirring bar, pressure equalizing addition funnel, and condenser with outlet tube on top connected to flare line was added 0.15 g of 50% aqueous NaOH, 1.06 g of Tergitol 15-S-7 ethoxylated alcohol (commercially available from Union Carbide Corporation) and 30.0 g of elemental sulfur (flowers of sulfur). To the addition funnel was added 135.3 g of t-butyl mercaptan. The mercaptan was added in portions to the reaction flask and when enough liquid was in the flask, it was stirred and heated to 50° C. Hydrogen sulfide evolved. After all the mercaptan was added, the reaction mixture was heated to and then held at 60° C. for 45 minutes. GC analysis (20 inch×⅛ in 2% OV-101 column, 50° C. initially, then 15° C./min, injection port temperature 150° C., FID detector) at this point showed that the reaction mixture consisted of 69.3% di-t-butyl trisulfide, 1.6% disulfide, 3.8% tetrasulfide, 0.1% pentasulfide, and 24.7% t-butyl mercaptan. For the polysulfide product alone without mercaptan, this would mean 92.0% trisulfide, 2.1% disulfide, 5.1% tetrasulfide, and 0.1% pentasulfide.

After cooling to near room temperature, 0.27 g of sulfuric acid solution (made from 1 part by weight concentrated $H_2SO_4$ and 2 parts water) was added and the reaction mixture was stirred. This amount of $H_2SO_4$ was just enough to neutralize the NaOH used in the procedure. The addition funnel and condenser were removed. The reaction flask was converted to a vacuum pump for vacuum distillation and the pressure was reduced to 400 torr. The reaction mixture was heated to 140° C. and maintained at 140° C. for 2 hours at 400 torr. Unreacted t-butyl mercaptan was collected in a trap for recycling. Then the pressure was raised back to atmospheric pressure and the reaction mixture was sparged with $N_2$ to remove the small amount of t-butyl mercaptan which was not removed in the vacuum distillation. The temperature during $N_2$ sparging was initially 120°–130° C. (1 hour) and later 100° C. (1.5 hours). After cooling, the reaction mixture was filtered to give 89.5 g of a clear yellow liquid. GC analysis, as described above, showed that the liquid consisted of 92.1% of di-t-butyl trisulfide, 2.1% disulfide, 5.4% tetrasulfide, 0.1% pentasulfide, and only a trace of t-butyl mercaptan (0.017%).

Comparison of these GC results with those given above show that after addition of $H_2SO_4$ and vacuum distillation and sparging, there was no change in the product except for loss of t-butyl mercaptan. A copper corrosion test using a 5% solution of the product in mineral oil at 100° C. for 3 hours resulted in a 1 b rating which showed the product was not corrosive (ASTM test method D130).

EXAMPLE II

This example illustrates the invention process using different quantities of catalyst component and sulfur.

The run was carried out the same was as described in Example I except that the amount of Tergitol 15-S-7 was reduced from 1.06 g to 0.80 g and the sulfur was reduced from 30.0 g to 27.0 g. The final product consisted of 84.2 g of a clear yellow liquid. GC analysis showed that the final product consisted of 91.0% of di-t-butyl trisulfide, 2.6% of di-t-butyl disulfide, 5.7% of di-t-butyl tetrasulfide, and 0.1% pentasulfide. the results were substantially similar to those of Example I. However, Example II suggests the use of more Tergitol 15-S-7 as in Example I gave slightly better results.

EXAMPLE III

This example is a comparative example illustrating an organic polysulfide was produced without the use of an acid.

The run was carried out the same way as described in Example I except that 33.0 g of sulfur was used and after heating at 60° C. for 0.5 hour, $H_2SO_4$ solution was not added before vacuum distillation. The vacuum distillation was carried out at 60° C. and 25 torr. GC analysis was performed each hour. The GC analyses are shown in the following Table I.

TABLE I

| Hours of vacuum distillation | Weight % by GC | | | | |
|---|---|---|---|---|---|
| | Disulfide | Trisulfide | Tetrasulfide | Pentasulfide | Mercaptan |
| 0 | 1.6 | 61.0 | 6.1 | 0.1 | 30.8 |
| 1 | 6.7 | 85.1 | 5.3 | 0.2 | 2.4 |
| 2 | 8.5 | 82.9 | 6.3 | 0.3 | 1.6 |
| 3 | 8.7 | 82.3 | 6.5 | 0.3 | 0.6 |

The results in Table I show that the product mixture changed with time, and the final mixture was lower in trisulfide and higher in disulfide when $H_2SO_4$ was not used to neutralize the NaOH, as compared with the results shown in Example I. These results also show that t-butyltrisulfide made without $H_2SO_4$ treatment was susceptible to decomposition during distillation even at lower temperature (60° C. in Example II and 140° C. in Example I).

EXAMPLE IV

This is a comparative example.

The run was carried out the same was as that described in Example I except that 33.0 g of sulfur was used, and after heating at 70° C. for 1 hour, $H_2SO_4$ was not added before vacuum distillation. The vacuum distillation was carried out at 70° C. and 100 torr and GC analyses were performed each hour. The results are shown in Table II.

TABLE II

| Hours of Vacuum distillation | Weight % by GC | | | | |
|---|---|---|---|---|---|
| | Disulfide | Trisulfide | Tetrasulfide | Pentasulfide | Mercaptan |
| 0 | 1.4 | 66.1 | 5.9 | 0.1 | 26.0 |
| 1 | 5.0 | 84.0 | 5.7 | 0.1 | 4.6 |
| 2 | 7.3 | 82.6 | 6.7 | 0.1 | 2.9 |
| 3 | 9.5 | 78.7 | 8.9 | 0.2 | 1.5 |

Similar to the results shown in Table I, when $H_2SO_4$ was not used to neutralize the NaOH, the trisulfide weight % decreased with increased time and was much lower than that obtained from the invention runs shown in Example I and II.

The results shown in the above examples clearly demonstrate that the present invention is well adapted to carry out the objects and attain the ends and advantages mentioned was well as those inherent therein. While modifications may be made by those skilled in the art, such modifications are encompassed within the spirit of the present invention as defined by the disclosure and the claims.

That which is claimed:

1. A process comprising contacting, in the presence of a catalyst, a mercaptan with elemental sulfur under a condition sufficient to produce a reaction medium containing a crude organic polysulfide and, thereafter, contacting said reaction medium with an acid; wherein said catalyst is a base; and said mercaptan, sulfur, and catalyst are each present in an amount effective to produce a crude organic polysulfide.

2. A process according to claim 1 wherein said polysulfide has a formula of R—$S_q$—R wherein each R is a hydrocarbyl radical having 1 to about 30 carbon atoms per molecule of said polysulfide and q is a number from 2 to about 10.

3. A process according to claim 2 wherein said hydrocarbyl radical has 2 to 15 carbon atoms per polysulfide molecule and q is a number from 3 to 5.

4. A process according to claim 1 wherein said organic polysulfide is a tertiary polysulfide.

5. A process according to claim 1 wherein said organic polysulfide is t-butyl trisulfide.

6. A process according to claim 1 wherein said catalyst is selected from the group consisting of inorganic bases, organic bases, and combinations of any two or more thereof.

7. A process according to claim 1 wherein said catalyst is selected from the group consisting of tetramethylammonium hydroxide, tetraethylammonium hydroxide, tetrapropylammonium hydroxide, tetramethylammonium bisulfide, tetraethylammonium bisulfide, lithium hydroxide, sodium hydroxide, sodium bisulfide, potassium hydroxide, potassium bisulfide, calcium hydroxide, magnesium hydroxide, sodium bicarbonate, sodium carbonate, sodium sulfide, sodium oxide, magnesium oxide, calcium oxide, calcium carbonate, sodium phenoxide, barium phenoxide, calcium phenoxide, $R^1ONa$, $R^1SNa$, and combinations of any two or more thereof; where $R^1$ is a $C_1$–$C_{18}$ alkyl radical, or combinations of any two or more thereof.

8. A process according to claim 1 wherein said catalyst is sodium hydroxide.

9. A process according to claim 6 wherein said catalyst comprises an alkoxylated compound selected from alkoxylated mercaptans, alkoxylated alcohols, and combinations of any two or more thereof.

10. A process according to claim 9 wherein said alkoxylated compound has the formula of $R^2O(CH_2CH_2O)_7H$ wherein $R^2$ is a secondary alkyl radical having 11 to 15 carbon atoms and 7 is the averaged number of the ethylene oxide units.

11. A process according to claim 1 wherein said acid is selected from the group consisting of sulfuric acid, hydrochloric acid, nitric acid, phosphoric acid, formic acid, acetic acid, trifluoroacetic acid, citric acid, trichloroacetic acid, p-toluenesulfonic acid, methanesulfonic acid, partially neutralized acids, and combinations of any two or more thereof.

12. A process according to claim 1 wherein said acid is sulfuric acid.

13. A process according to claim 1 wherein the amount of said acid is about 0.5 to about 2 equivalents of said catalyst.

14. A process according to claim 1 wherein the amount of said acid is about 0.9 to about 1.1 equivalents of said catalyst.

15. A process according to claim 1 wherein the amount of said acid is equal equivalent of said catalyst.

16. A process for producing an organic polysulfide comprising contacting, in the presence of a catalyst, a mercaptan with elemental sulfur to produce a reaction medium which comprises said organic polysulfide and thereafter contacting said reaction medium containing said organic polysulfide with an acid to produce an acid-treated organic polysulfide wherein:

said organic polysulfide has the formula of $R-S_q-R$;

said catalyst is not an alkylamine and is selected from the group consisting of inorganic bases and organic bases, and combinations of any two or more thereof;

said mercaptan has the formula of RSH; and said acid is selected from the group consisting of sulfuric acid, hydrochloric acid, nitric acid, phosphoric acid, formic acid, acetic acid, trifluoroacetic acid, citric acid, trichloroacetic acid, p-toluenesulfonic acid, methanesulfonic acid, partially neutralized acids, and combinations of any two or more thereof;

each R is a hydrocarbyl radical having 1 to about 30 carbon atoms; and q is a number from 2 and about 10.

17. A process according to claim 16 wherein:

said catalyst is selected from the group consisting of tetramethylammonium hydroxide, tetraethylammonium hydroxide, tetrapropylammonium hydroxide, tetramethylammonium bisulfide, tetraethylammonium bisulfide, lithium hydroxide, sodium hydroxide, potassium hydroxide, calcium hydroxide, magnesium hydroxide, sodium bicarbonate, sodium carbonate, sodium oxide, magnesium oxide, calcium oxide, calcium carbonate, sodium phenoxide, barium phenoxide, calcium phenoxide, $R^1ONa$, $R^1SNa$, and combinations of any two or more thereof; where $R^1$ is a $C_1-C_{18}$ alkyl radical, or combinations of any two or more thereof;

said mercaptan is a tertiary mercaptan;

said acid is sulfuric acid;

each R is a hydrocarbyl radical having 1 to about 20 carbon atoms; and q is a number from 2 to 8.

18. A process according to claim 17 wherein said catalyst further comprises an alkoxylated alcohol.

19. A process according to claim 17 wherein said catalyst is a mixture of sodium hydroxide and an ethoxylated alcohol having a formula of $R^2O(CH_2CH_2O)_7H$ wherein $R^2$ is a secondary alkyl radical having 11 to 15 carbon atoms and 7 is the averaged number of the ethylene oxide units; each R is a hydrocarbyl radical having 2 to 15 carbon atoms; and q is a number from 3 to 5.

20. A process according to claim 19 wherein said organic polysulfide is t-butyl trisulfide.

21. A process for producing t-butyl trisulfide comprising contacting, in the presence of a mixture of sodium hydroxide and an ethoxylated alcohol having a formula of $R^2O(CH_2CH_2O)_7H$ wherein $R^2$ is a secondary alkyl radical having 11 to 15 carbon atoms and 7 is the averaged number of the ethylene oxide units, t-butyl mercaptan with elemental sulfur to produce a reaction medium containing said t-butyl trisulfide and contacting said reaction medium with sulfuric acid to produce an acid-treated t-butyl trisulfide.

22. A process according to claim 21 further comprising recovering said acid-treated butyl trisulfide.

* * * * *